United States Patent
Banju et al.

(10) Patent No.: US 10,858,624 B2
(45) Date of Patent: Dec. 8, 2020

(54) FILTER FOR FILTERING NUCLEATED CELLS AND FILTERING METHOD USING THE SAME

(71) Applicant: Murata Manufacturing Co., Ltd., Nagaokakyo (JP)

(72) Inventors: Masaru Banju, Nagaokakyo (JP); Junko Watanabe, Nagaokakyo (JP); Takashi Kondo, Nagaokakyo (JP); Seiichi Matsumoto, Nagaokakyo (JP)

(73) Assignee: MURATA MANUFACTURING CO., LTD., Nagaokakyo (JP)

( * ) Notice: Subject to any disclaimer, the term of this patent is extended or adjusted under 35 U.S.C. 154(b) by 0 days.

(21) Appl. No.: 15/905,056

(22) Filed: Feb. 26, 2018

(65) Prior Publication Data

US 2018/0312803 A1    Nov. 1, 2018

(30) Foreign Application Priority Data

Apr. 26, 2017    (JP) .................................. 2017-087511

(51) Int. Cl.
*B01D 67/00* (2006.01)
*B01D 69/10* (2006.01)
(Continued)

(52) U.S. Cl.
CPC ........... *C12N 5/0087* (2013.01); *B01D 39/10* (2013.01); *B01D 61/147* (2013.01); *B01D 67/0062* (2013.01); *B01D 69/02* (2013.01); *B01D 71/022* (2013.01); *B01D 71/024* (2013.01); *G01N 33/491* (2013.01); *B01D 2325/021* (2013.01)

(58) Field of Classification Search
None
See application file for complete search history.

(56) References Cited

U.S. PATENT DOCUMENTS 4,894,343 A * 1/1990 Tanaka ................... C12M 23/20
                                                                210/498
6,491,819 B2   12/2002 Prince et al.
(Continued)

FOREIGN PATENT DOCUMENTS

DE    202012003212 U1    7/2012
EP        3031903 A1    6/2016
(Continued)

OTHER PUBLICATIONS

Kantak et al., Lab-on-a-chip technology: impacting non-invasive prenatal diagnostics (NIPD) through miniaturization, 14 Lab Chip, 841, 843 (2014). (Year: 2014).*
(Continued)

*Primary Examiner* — Krishnan S Menon
*Assistant Examiner* — Brad Gordon
(74) *Attorney, Agent, or Firm* — Arent Fox LLP (57) ABSTRACT

A filter for filtering nucleated cells that includes a body containing at least either a metal or a metal oxide as its main component; and plural through holes, each of which have a shape other than a square shape, formed therein. A longitudinal diameter of an inscribed ellipse within each of the through holes is smaller than a size of a nucleus of each of the nucleated cells to be filtered. The inscribed ellipse of the through hole is an ellipse that abuts all sides that define an opening of the through hole.

15 Claims, 6 Drawing Sheets

(51) Int. Cl.
  *B01D 71/02*  (2006.01)
  *B01D 61/14*  (2006.01)
  *B01D 69/02*  (2006.01)
  *G01N 33/49*  (2006.01)
  *C12N 5/00*  (2006.01)
  *B01D 39/10*  (2006.01)

(56) References Cited

U.S. PATENT DOCUMENTS

| | | |
|---|---|---|
| 6,497,821 B1 | 12/2002 | Bellamy, Jr. et al. |
| 8,273,253 B2 | 9/2012 | Curran |
| 8,777,017 B2 | 7/2014 | Curran |
| 9,291,533 B2 | 3/2016 | Prins et al. |
| 2002/0033367 A1 | 3/2002 | Prince et al. |
| 2004/0142463 A1* | 7/2004 | Walker .................. A61M 1/36 435/325 |
| 2006/0252044 A1* | 11/2006 | Okumura .......... G01N 33/54373 435/6.11 |
| 2006/0254972 A1 | 11/2006 | Tai et al. |
| 2009/0269812 A1 | 10/2009 | Sawai et al. |
| 2010/0143879 A1 | 6/2010 | Curran |
| 2011/0177551 A1 | 7/2011 | Mimitsuka et al. |
| 2013/0098827 A1 | 4/2013 | Curran |
| 2013/0264268 A1 | 10/2013 | Yoshioka et al. |
| 2013/0264272 A1 | 10/2013 | Jeon et al. |
| 2014/0147883 A1 | 5/2014 | Prins et al. |
| 2015/0111293 A1 | 4/2015 | Kanbara et al. |
| 2015/0129769 A1 | 5/2015 | Kamba et al. |
| 2015/0247802 A1* | 9/2015 | Ozasa ................ G01N 15/1429 435/6.15 |
| 2016/0041075 A1 | 2/2016 | Kamba et al. |
| 2016/0054223 A1 | 2/2016 | Kamba et al. |
| 2016/0168601 A1 | 6/2016 | Mimitsuka et al. |
| 2017/0137769 A1* | 5/2017 | Kikuhara ............. G01N 33/491 |
| 2017/0247662 A1 | 8/2017 | Kanbara et al. |
| 2017/0282180 A1 | 10/2017 | Yagi et al. |

FOREIGN PATENT DOCUMENTS

| | | |
|---|---|---|
| JP | H2-43911 A | 2/1990 |
| JP | 2000-501338 A | 2/2000 |
| JP | 2005-152527 A | 6/2005 |
| JP | 2007252367 A | 10/2007 |
| JP | 2008-23469 A | 2/2008 |
| JP | 2008048721 A | 3/2008 |
| JP | 2008237213 A | 10/2008 |
| JP | 2009-284860 A | 12/2009 |
| JP | 2010-520446 A | 6/2010 |
| JP | 2013-215109 A | 10/2013 |
| JP | 2013-541958 A | 11/2013 |
| JP | 2013-255487 A | 12/2013 |
| JP | 2014-523534 A | 9/2014 |
| JP | 2015-192642 A | 11/2015 |
| JP | 2016-52300 A | 4/2016 |
| JP | 2016-86736 A | 5/2016 |
| JP | 2016103982 A | 6/2016 |
| WO | 2007097260 A1 | 8/2007 |
| WO | 2010038613 A1 | 4/2010 |
| WO | WO 2013/172265 A1 | 11/2013 |
| WO | WO 2014/017430 A1 | 1/2014 |
| WO | WO 2014/192389 A1 | 12/2014 |
| WO | WO 2014/192917 A1 | 12/2014 |
| WO | WO-2015145793 A1 * | 10/2015 |
| WO | 2016031971 A1 | 3/2016 |
| WO | 2016140005 A1 | 9/2016 |
| WO | 2016158793 A1 | 10/2016 |

OTHER PUBLICATIONS

Medical equipment News: "Murata PM 2.5 can also be detected, Murata Manufacturing unveils standard products of metal mesh devices"; <http://monoist.atmarkit.co.jp/mn/articles/1409/03/news128.html> (Retreived Apr. 30, 2018).

* cited by examiner

FILTER FOR FILTERING NUCLEATED CELLS AND FILTERING METHOD USING THE SAME

CROSS REFERENCE TO RELATED APPLICATIONS

The present application claims priority to Japanese Patent application No. 2017-087511, filed Apr. 26, 2017, the entire contents of which are incorporated herein by reference.

FIELD OF THE INVENTION

The present invention relates to a filter for filtering nucleated cells and a filtering method using the filter.

BACKGROUND OF THE INVENTION

Patent Document 1 discloses a method for concentrating mono-nucleated cells and blood platelets using a cell trapping filter material from a liquid containing red blood cells, nucleated cells, and blood platelets. The cell trapping filter material of Patent Document 1 traps the nucleated cells and the blood platelets and causes the unnecessary cells such as the red blood cells to pass therethrough.

Patent Document 1: Japanese Laid-Open Patent Publication No. 2009-284860

SUMMARY OF THE INVENTION

The cell trapping filter material of Patent Document 1 still has room for improvement in relation to the point of improvement of the collection rate of the nucleated cells.

An object of the present invention is to provide a filter for filtering nucleated cells that can improve the collection rate of nucleated cells, and a filtering method using the filter.

A filter for filtering nucleated cells according to an aspect of the present invention includes a filter body containing at least either a metal or a metal oxide as a main component thereof, and defining a plurality of through holes therein, each of the plurality of through holes having a shape other than a square shape. A longitudinal diameter of an inscribed ellipse within each of the plurality of through holes is smaller than the size of the nucleus of each of the nucleated cells to be filtered, and the inscribed ellipse of the through hole is an ellipse abutting all the sides that define the opening of the through hole.

A filtering method for filtering nucleated cells according to an aspect of the present invention includes preparing a filter body that includes at least either a metal or a metal oxide as a main component thereof and defines a plurality of through holes therein, each of the plurality of through holes having a shape other than a square shape, wherein the longitudinal diameter of an inscribed ellipse within each of the through holes being smaller than the size of a nucleus of each of the nucleated cells, and the inscribed ellipse of the through hole being an ellipse abutting all the sides that define the opening of the through hole; and causing a liquid containing the nucleated cells to pass through the plurality of through holes of the filter body.

According to the present invention, there can be provided a filter for filtering nucleated cells that can improve the collection rate of nucleated cells, and a filtering method that uses the filter.

DETAILED DESCRIPTION OF THE INVENTION

In Patent Document 1, mono-nucleated cells are separated from blood by trapping nucleated cells and blood platelets using a cell trapping filter that includes a non-woven cloth and causing unnecessary cells such as red blood cells to pass therethrough. With the cell trapping filter of Patent Document 1, the collection rate of the mono-nucleated cells is however about 74% and the cell trapping filter still has room for improvement in relation to the point of improvement of the collection rate of the cells to be trapped.

The inventors have actively studied and found that the collection rate of the nucleated cells to be trapped was able to be improved by conducting filtering for a liquid that included the nucleated cells, using a filter including at least either a metal or a metal oxide as its main component.

A filter for filtering nucleated cells according to an aspect of the present invention includes a base comprising at least either a metal or a metal oxide as its main component, and a plurality of through holes (each having a shape other than a square shape) that are formed therein, wherein the longitudinal diameter of an inscribed ellipse of each of the through holes is smaller than the size of the nucleus of each of the nucleated cells, and the inscribed ellipse of the through hole is an ellipse abutting all the sides that define the opening of the through hole.

With this configuration, the collection rate of the nucleated cells can be improved.

In the filter, the shape of the through hole may be a polygonal shape so as to further improve the collection rate of the nucleated cells.

In the filter, the shape of the through hole may be a rectangular shape.

With such a configuration, the time period for filtering can be reduced and the collection rate of the nucleated cells can be improved.

The filter may further include a filter part that includes the plurality of through holes penetrating a first principal surface and a second principal surface that face each other, and a frame part that is arranged to surround the outer circumference of the filter part, wherein in the filter part, a film thickness of the filter part in a region on the side of the center that is distant from the frame part may be smaller than a film thickness of the filter part in a region on the side of a peripheral edge that is closer to the frame part than to the region on the side of the center.

With this configuration, a concave face can be formed in a portion of the surface of at least either the first principal surface or the second principal surface of the filter part. When cells are trapped on the side having the concave face formed thereon, a fluid reservoir tends to be formed in the concave face due to the surface tension of the fluid and any drying of the trapped cells can therefore be suppressed. Handling convenience of the cells trapped by the filter part can therefore be improved.

For the filter, at least either the metal or the metal oxide may have an immersion potential in a phosphate buffered physiological saline solution that is nobler than 0.03 V relative to a reference electrode including silver chloride immersed in a saturated potassium chloride solution.

With this configuration, any elution of the metal or the metal oxide component of the filter into the solution containing the nucleated cells can be prevented.

For the filter, at least either the metal or the metal oxide may include at least one selected from gold, silver, copper, platinum, nickel, palladium, an alloy thereof, and an oxide thereof.

With this configuration, the collection rate of the nucleated cells can further be improved.

A filtering method of an aspect of the present invention includes preparing a filter including at least either a metal or a metal oxide as its main component, and having a plurality of through holes (each having a shape other than a square shape) formed therein, and the longitudinal diameter of an inscribed ellipse of each of the through holes is smaller than the size of a nucleus of each of the nucleated cells and the inscribed ellipse of the through hole is an ellipse butting all the sides that define an opening of the through hole, and causing a liquid containing the nucleated cells to pass through the filter.

With this configuration, the collection rate of the nucleated cells can be improved.

For the filtering method, the shape of the through hole may be a polygonal shape. With such a configuration, the collection rate of the nucleated cells can be improved.

For the filtering method, the shape of the through hole may be a rectangle. With such a configuration, the time period for the filtering can be reduced and the collection rate of the nucleated cells can further be improved.

For the filtering method, the filter may include a filter part that includes the plurality of through holes penetrating a first principal surface and a second principal surface that face each other, and a frame part arranged to surround the outer circumference of the filter part. In the filter part, a film thickness of the filter part in a region on the side of the center that is distant from the frame part may be smaller than a film thickness of the filter part in a region on the side of a peripheral edge that is closer to the frame part than to the region on the side of the center.

With this configuration, the cells can be trapped by a concave face formed in a portion of the surface of at least either the first principal surface or the second principal surface of the filter part. A fluid reservoir tends to be formed in the concave face due to the surface tension of the fluid and any drying of the trapped cells can therefore be suppressed. Handling convenience of the cells trapped by the filter part can be improved.

For the filtering method, at least either the metal or the metal oxide may have an immersion potential in a phosphate buffered physiological saline solution that is nobler than 0.03 V relative to a reference electrode including silver chloride, immersed in a saturated potassium chloride solution.

With this configuration, any elution of the metal or the metal oxide component of the filter into the liquid containing the nucleated cells can be presented.

For the filtering method, the at least either the metal or the metal oxide may include at least one selected from gold, silver, copper, platinum, nickel, palladium, an alloy thereof, and an oxide thereof.

With this configuration, the collection rate of the nucleated cells can further be improved.

For the filtering method, the causing the liquid containing the nucleated cells to pass through the filter may include separating living cells and dead cells from each other.

With this configuration, living cells and dead cells can be separated from each other.

A first embodiment according to the present invention is described below with reference to the accompanying drawings. In the drawings, elements are depicted being exaggerated to facilitate the description.

First Embodiment

[Configuration of Filter]

Figure 1:
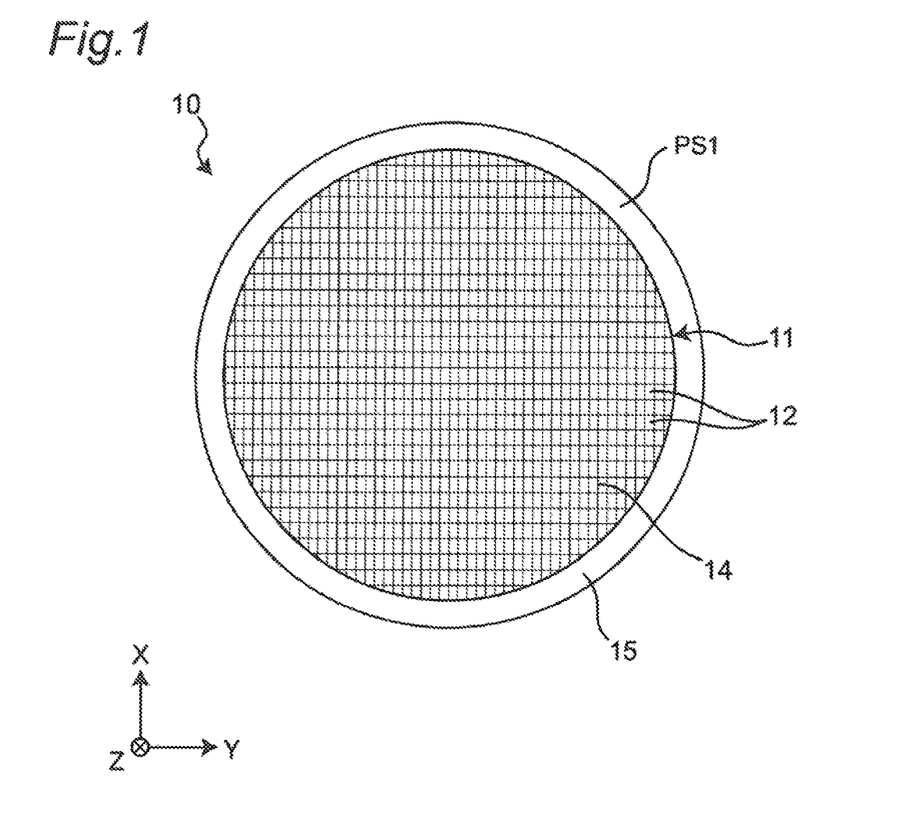
FIG. 1 is a schematic configuration diagram of a filter of a first embodiment according to the present invention.
Figure 2:
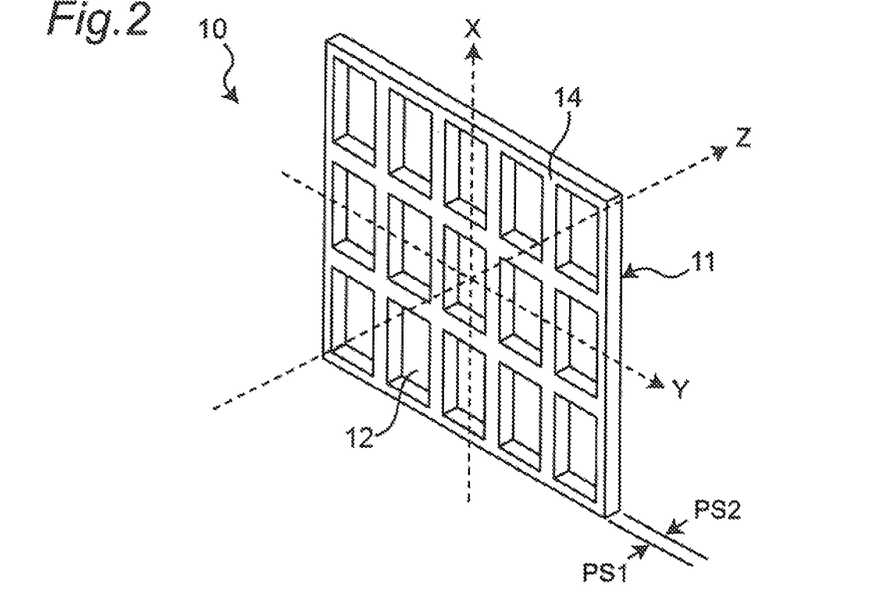
FIG. 2 is an enlarged perspective diagram of a portion of the filter of the first embodiment according to the present invention.

FIG. 1 is a schematic configuration diagram of a filter 10 of the first embodiment according to the present invention. FIG. 2 is an enlarged perspective diagram of a portion of the filter 10 of the first embodiment according to the present invention. A X-, a Y-, and a Z-directions in FIG. 1 and FIG. 2 respectively indicate a longitudinal direction, a lateral direction, and a thickness direction of the filter 10. As depicted in FIG. 1, the filter 10 includes a filter part 11 and a frame part 15 disposed on the outer circumference of the filter part 11. As depicted in FIG. 2, the filter 10 includes a first principal surface PS1 and a second principal surface PS2 that face each other. The filter part 11 includes filter base body parts 14 formed therein that have plural through holes 12 formed therein that penetrate the first principal surface PS1 and the second principal surface PS2.

The filter 10 filters nucleated cells by causing a liquid containing nucleated cells (a cell suspension) to pass through the filter part 11.

In this specification, the "nucleated cell" refers to a cell whose nuclear body and cytoplasm are isolated from each other by a nuclear membrane.

<Material>

The material constituting the filter base body parts 14 forming the base body portion of the filter 10 includes a metal and/or a metal oxide as its main component. The filter base body parts 14 may be gold, silver, copper, platinum, nickel, palladium, an alloy thereof, and an oxide thereof.

The outer surface layer of the filter 10 may include a metal and/or a metal oxide that tend(s) to avoid being eluted into the cell suspension. For example, when the outer surface layer of the filter 10 is covered with a metal whose immersion potential in a phosphate buffered physiological saline solution is nobler than 0.03 V relative to a reference electrode including silver chloride immersed in a saturated potassium chloride solution, any elution of the material constituting the filter 10 into the cell suspension can be suppressed. This can reduce any stress applied to the cells. Otherwise, the outer surface layer of the filter 10 may include a hydrophilic material. For example, when a water-based cell suspension is treated, the time period for the treatment can be reduced and any stress applied to the cells can therefore be reduced.

<Outer Shape>

The outer shape of the filter 10 is, for example, a circular, a rectangular, or an ellipsoidal shape. In the first embodiment, the outer shape of the filter 10 is a substantially circular shape. Any fluid can be caused to uniformly flow to the principal surface of the filter 10 (for example, the first principal surface PS1 of the filter part 11) by setting the outer shape of the filter 10 to be the substantially circular shape. In this specification, the "substantially circular shape" refers to the fact that the ratio of the length of the longitudinal diameter to the length of the lateral diameter is 1.0 to 1.2.

<Filter Part>

The filter part 11 is a plate-like structure that has a plurality of through holes 12 formed therein. The shape of the filter part 11 is, for example, a circular, a rectangular, or an ellipsoidal shape. In the first embodiment, the shape of the filter part 11 is a substantially circular shape. Any fluid can be caused to uniformly flow to the first principal surface PS1 of the filter part 11 by setting the shape of the filter part 11 to be the substantially circular shape.

Figure 3:
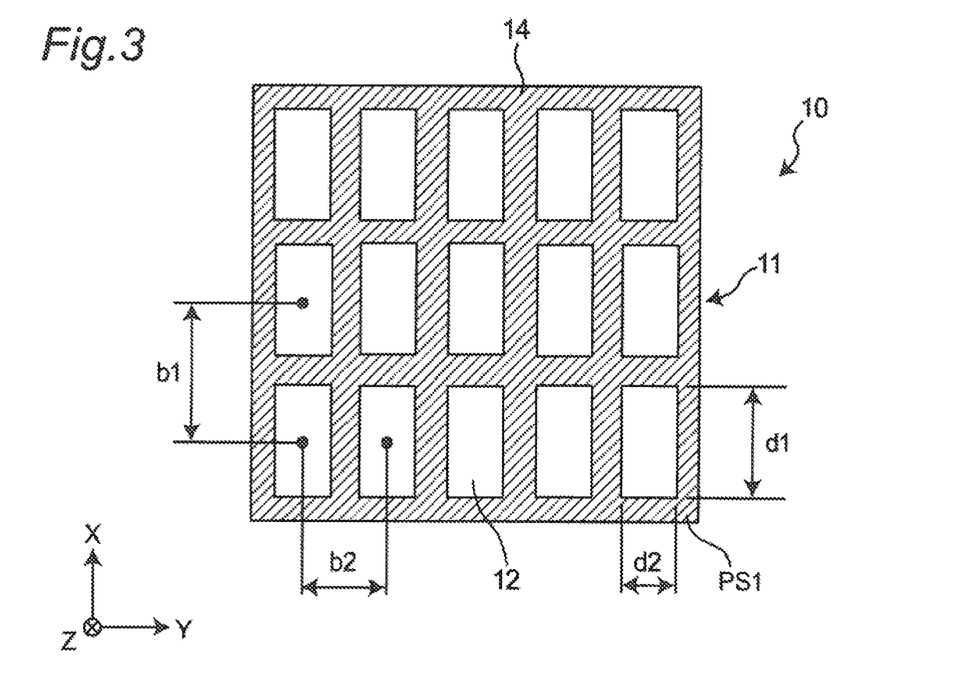
FIG. 3 is a schematic diagram of the portion of the filter of FIG. 2 seen from the thickness direction.

FIG. 3 is a schematic diagram of a portion of the filter part 11 seen from a thickness direction (the Z-direction). As depicted in FIG. 3, the plural through holes 12 are cyclically arranged on the first principal surface PS1 and the second principal surface PS2 of the filter part 11. For example, the plural through holes 12 are disposed at equal intervals in a matrix-like form in the filter part 11.

In the first embodiment, the through holes 12 each have a rectangular shape seen from the side of the first principal surface PS1 of the filter part 11, that is, the Z-direction. As depicted in FIG. 3, the shape of the through hole 12 is the rectangular shape whose long sides d1 are in the X-direction and whose short sides d2 are in the Y-direction. The through hole 12 has the shape other than a square shape seen from the Z-direction. The through hole 12 may have a shape such as, for example, a lozenge shape or any one of polygonal shapes. The polygonal shapes may include regular polygonal shapes except the square shape.

In the first embodiment, the long side d1 of the through hole 12 is formed to have, for example, greater than a 1.2-fold length and equal to or smaller than a 1.8-fold length of the length of the short side d2.

In the first embodiment, the shape of the through hole 12 projected onto a plane that is perpendicular to the first principal surface PS1 of the filter part 11 (the cross-sectional shape) is a rectangular shape. For example, the cross-sectional shape of the through hole 12 is a rectangular shape whose one side in the radius direction of the filter 10 has a length that is longer than the length of one side in the thickness direction of the filter 10. The cross-sectional shape of the through hole 12 is not limited to the rectangular shape and may be, for example, a parallelogram shape or a tapered shape such as a trapezoidal shape, may be a symmetrical shape, or may be an asymmetrical shape.

In the first embodiment, the plural through holes 12 are disposed at equal intervals in two arrangement directions parallel to the sides of the rectangle seen from the side of the first principal surface PS1 (the Z-direction) of the filter part 11, that is, the X-direction and the Y-direction in FIG. 3. The aperture ratio can be increased and the passage resistance of a fluid against the filter 10 can be reduced by disposing the plural through holes 12 in rectangular grid arrangement as above. With this configuration, the time period for the treatment can be reduced and any stress applied to the cells can be reduced. Because the symmetry of the arrangement of the plural through holes 12 is improved, observation of the filter is facilitated.

The arrangement of the plural through holes 12 is not limited to the rectangular grid arrangement and may be, for example, quasi-cyclic arrangement or cyclic arrangement. Rectangular arrangement whose intervals are not equal between the two arrangement directions may be employed as the quadrate arrangement as examples of the cyclic arrangement, or triangular grid arrangement, equilateral-triangular grid arrangement, or the like may be employed. The plural through holes 12 only have to be disposed in the filter part 11 and the arrangement thereof is not limited.

The corner portions each connecting the sides that define the opening of the through hole 12 to each other may be R-processed. That is, the corner portions of the through holes 12 may each be formed to be round. With this configuration, any damage to the cells can be suppressed in the corner portions of the through holes 12 and the activity of the cells can further be maintained.

The intervals of the through holes 12 are properly designed in accordance with the type of the cells to be separated (the size, the form, the properties, and the elasticity) or the amount thereof. The "intervals of the through holes 12" mean distances b1 and b2 each between the center of an optional through hole 12 and the center of the through hole 12 adjacent thereto as depicted in FIG. 3 when the through holes 12 are seen from the side of the first principal surface PS1 of the filter part 11. For example, the interval b1 means the distance between the center of the through hole 12 and the center of the through hole 12 adjacent thereto in the direction of the short side (the X-direction) of the through hole 12. The interval b2 means the distance between the center of the through hole 12 and the center of the through hole 12 adjacent thereto in the direction of the long side (the Y-direction) of the through hole 12. In the first embodiment, "the center of the optional through hole 12" means the intersection of the diagonal lines of the through hole 12 having the rectangular shape.

For the structure having the cyclical arrangement, the intervals b1 of the through holes 12 each have, for example, a length longer than a one-fold length of the long side d1 of the through hole 12 and equal to or shorter than a ten-fold length thereof and, preferably, each have a length equal to or shorter than a three-fold length of the long side d1 of the through hole 12. The intervals b2 of the through holes 12 each have, for example, a length longer than a one-fold length of the short side d2 of the through hole 12 and equal to or shorter than a 10-fold length thereof and, preferably, each have a length equal to or shorter than a three-fold length of the short side d2 of the through hole 12. Otherwise, for example, the aperture ratio of the filter part 11 is equal to or greater than 10% and, preferably, the aperture ratio is equal to or greater than 25%. With this configuration, the passage resistance of a fluid against the filter part 11 can be reduced. The time period for the treatment can therefore be reduced and any stress applied to the cells can be reduced. The "aperture ratio" is calculated by (the area occupied by the through holes 12)/(the projected area of the first principal surface PS1 acquired when it is assumed that no through hole 12 is formed).

The longitudinal diameter of an inscribed ellipse of the through hole 12 is designed to be smaller than the size of the nucleus of the nucleated cell. In this specification, the "inscribed ellipse of the through hole 12" means an ellipse that has a longitudinal diameter and a lateral diameter and that has the largest longitudinal diameter of the ellipses capable of being drawn in the through hole 12, seen from the side of the first principal surface PS1 of the filter part 11. The "inscribed ellipse of the through hole 12" means an ellipse that has the largest longitudinal diameter of the ellipses each butting the inner wall of the filter base body part 14 constituting the through holes 12. In other words, the "inscribed ellipse of the through hole 12" means an ellipse that butts all the sides defining the opening of the through hole 12 seen from the side of the first principal surface PS1 of the filter part 11. The longitudinal diameter and the lateral diameter of the "inscribed ellipse of the through hole 12" may have different lengths or may have the equal length. In this specification, the "inscribed ellipse of the through hole 12" may include an exact circle.

In this specification, the "size of the nucleus of a nucleated cell" means the average value of the lengths of the nuclei of plural nucleated cells that is acquired when the nucleated cells are arranged in a liquid and are observed using a microscope and the longest line of lines each connecting optional two points on the outer circumference of the nucleus of the nucleated cell is defined as the length of the nucleus.

The dimensions of the plural through holes 12 are designed to substantially be equal. When the configuration is employed that having the plural through holes 12 cyclically arranged therein that have the same shape, preferably, the standard deviation of the size of the plural through holes 12 is small.

The filter part 11 has a film thickness that is uniform from the center of the filter part 11 toward the outer side thereof. In other words, when the filter part 11 is cut in the Z-direction of the filter part 11, the filter part 11 has a flat plate-like cross-sectional shape. Preferably, the thickness of the filter part 11 is greater than a 0.1-fold length of the shortest side (for example, the short side d2) of the sides defining the through hole 12 and is equal to or smaller than a 100-fold length thereof. More preferably, the thickness of the filter part 11 is greater than a 0.5-fold length of the short side d2 of the through hole 12 and equal to or smaller than a 10-fold length thereof. With this configuration, the resistance of the filter 10 against a fluid can be reduced and the time period for the treatment can be reduced. As a result, any stress applied to the cells can be reduced.

Preferably, the arithmetic average roughness of the surface of the filter part 11 (the first principal surface PS1) is smaller than the size of the nucleus of the nucleated cell. With this configuration, any adhesion of the cells to the surface of the filter part 11 (the first principal surface PS1) is reduced and the collection rate of the cells can be increased. For the measurement of the arithmetic average roughness, a stylus profile meter DEKTAK 150 (a registered trademark) manufactured by ULVAC, Inc., was used and the average value of the measurements acquired at five points on the surface of the filter part 11 was taken as the arithmetic average roughness of the filter part 11.

In the filter part 11, the first principal surface PS1 in contact with the liquid containing the nucleated cells may be formed to be flat and smooth. For example, the first principal surface PS1 of the filter part 11 may be formed to be a uniform flat face that has no recess and no protrusion. In other words, the openings of the plural through holes 12 in the first principal surface PS1 of the filter part 11 are formed in the same one plane. The filter base body parts 14 to be the portion having no through hole 12 formed therein of the filter part 11 are continuous and are integrally formed. With this configuration, any adhesion of the cells to the surface of the filter part 11 (the first principal surface PS1) is reduced and the trapped nucleated cells can easily be collected.

As to each of the through holes 12 of the filter part 11, its opening on the side of the first principal surface PS1 and its opening on the side of the second principal surface PS2 communicate with each other through a continuous wall face. For example, the through hole 12 is disposed such that the opening on the side of the first principal surface PS1 can be projected onto the opening on the side of the second principal surface PS2. The through hole 12 is provided such that the opening on the side of the first principal surface PS1 overlaps with the opening on the side of the second principal surface PS2 when the filter part 11 is seen from the side of the first principal surface PS1. In the first embodiment, the through hole 12 is disposed such that the inner wall thereof is perpendicular to the first principal surface PS1 and the second principal surface PS2.

<Frame Part>

The frame part 15 is disposed on the outer circumference of the filter part 11 and is a portion whose number of the through holes 12 per unit area is small compared to that of the filter part 11. The number of the through holes 12 in the frame part 15 is equal to or smaller than 1% of the number of the through holes 12 in the filter part 11. The thickness of the frame part 15 may be greater than the thickness of the filter part 11. With this configuration, the mechanical strength of the filter 10 can be enhanced.

When the filter 10 is used and connected to an apparatus, the frame part 15 may function as a connecting part that connects the filter 10 and the apparatus to each other. The frame part 15 may have information of the filter (such as the dimensions of the through holes 12) displayed thereon.

The frame part 15 is formed to have a ring-like shape, seen from the side of the first principal surface PS1 of the filter part 11. The center of the frame part 15 matches with the center of the filter part 11 when the filter 10 is seen from the side of the first principal surface PS1. The frame part 15 is formed on a concentric circle of the filter.

From the viewpoint of handling convenience and easiness of joining with a system, the filter 10 may be fixed on a jig. The jig can be constituted using, for example, a material capable of being gamma-sterilized. The jig may be formed using a material that includes, for example, polyethylene, polyethyleneterephthalate, polyurethane, polystyrene, silicon rubber, an ABS resin, polyamide, polyamideimide, polysulphone, natural rubber, latex, urethane rubber, ethylene-vinyl acetate, polyesters, epoxys, phenols, silica, alumina, gold, platinum, nickel, stainless steel, or titanium. Any stress applied to the cells can be reduced by constituting the jig using the above material.

[Filtering Method]

A filtering method using the filter 10 will be described.

The filter 10 is first prepared. At this step, the filter 10 is prepared whose through holes 12 have the size selected in accordance with the size of the nucleus of each of the nucleated cells. For example, the filter 10 is prepared that includes the through holes 12 each being smaller than the size of the nucleus of each of the nucleated cells to be filtered.

For example, at the step of preparing the filter 10, the filter 10 whose through holes 12 each have the size smaller than the size of the nucleus of each of the nucleated cells may be selected by checking the sizes of the nuclei of plural ones of the nucleated cells using a micrometer or a hemocytometer. Otherwise, the filter 10 whose through holes 12 each have the size smaller than the size of the nucleus of each of the nucleated cells may be selected by taking a photograph of plural ones of the nucleated cells and measuring thereon the size/length of the nucleus of each of the plural ones of the nucleated cells. The selection of the filter 10 is not limited to the above.

The filter 10 is attached to an apparatus. For example, the filter 10 is attached to the apparatus by holding and pinching the frame part 15 of the filter 10.

A cell suspension is caused to pass through the filter 10. In this specification, the "cell suspension" refers to a fluid that contains nucleated cells. In many cases, the fluid containing the nucleated cells is a liquid. Examples of the liquid include, for example, a culture solution containing an amino acid, a protein, a serum, the like, a phosphate buffered physiological saline solution, or water. The cell suspension may contain a non-biological material such as a resin particle, a portion of a tissue such as a bone fragment or a meat piece, and dead cells, in addition to the cells and the fluid.

The nucleated cells are separated from the liquid by causing the liquid containing the nucleated cells to pass through the filter part 11 as above. In the first embodiment, the longitudinal diameter of the inscribed ellipse of the through hole 12 of the filter part 11 is designed to be smaller than the size of the nucleus of each of the nucleated cells. The nucleated cells therefore do not pass through the through holes 12 and are trapped on the first principal surface PS1 of the filter part 11.

Examples of the method of causing the cell suspension to pass through the filter 10 include, for example, a method of causing the cell suspension to pass through the first principal surface PS1 of the filter part 11 from above to be substantially perpendicular thereto using the gravitational force. In addition, a method is present according to which the cell suspension is brought into contact with the first principal surface PS1 of the filter part 11 and is thereafter pressured to be caused to pass therethrough (pressurizing) or a method is present according to which the cell suspension is brought into contact with the first principal surface PS1 of the filter part 11 and is thereafter suctioned from the second principal surface PS2 to be caused to pass therethrough (suction). Preferably, any stress applied to the cells is avoided as far as possible at the step of causing the liquid containing the nucleated cells to pass through the filter part 11. For example, when the pressure is applied, preferably, the pressure is set to the extent that the nucleated cells are not deformed. More preferably, the liquid is caused to pass through the filter part 11 using the liquid's own weight without applying any pressure thereto. Otherwise, preferably, the time period for the treatment is reduced by increasing the aperture ratio of the filter part 11 and the time period is thereby reduced during which a stress is applied to the nucleated cells.

The cell suspension may be caused to pass through the filter 10 in the state where the nucleated cells are suspended in the liquid. Because the nucleated cells suspended in the liquid each take a substantially spherical shape, the collection rate of the nucleated cells to be trapped can be improved. The dimension precision of the nucleated cells desired to be trapped can be improved.

The dimension precision of the nucleated cells to be trapped can be improved by causing the cell suspension to pass through the filter 10 for plural times.

For the filtering method using the filter 10, the filtering may be conducted using, for example, a container for filtering. The container for filtering is, for example, a cylindrical container having an outer diameter of 14 mm, an inner diameter of 6 mm, and a height of 55 mm, and the filter 10 can be attached to the bottom portion of the container. The container for filtering is not limited to the above and any one of containers having various shapes and various dimensions may be used.

[Manufacturing Method for Filter]

A typical manufacturing method for the filter 10 will be described. The filter 10 is manufactured at the following steps.

<Formation of Power Supply Film>

A power supply film made from Cu is formed on the upper face of a silicon substrate using a sputtering apparatus. The power supply film acts as a power supply source used when the filter base body parts 14 (described later) of the filter 10 are formed. In this case, an intermediate layer made from Ti or the like may be formed aiming at securing the adhesiveness between the silicon substrate and the power supply film.

The conditions for forming the Cu power supply film are as follows.

Sputtering Gas: An argon gas
Degree of Vacuum of Sputtering Apparatus: $5.0 \times 10^{-4}$ Pa
Applied Power: DC 500 W
Sputtering Time Period: For forming a Cu film/27 min
For forming a Ti film/3 min and 5 sec <Formation of Resist Image>

A resist image is formed on the power supply film formed on the upper face of the silicon substrate.

A resist film having a predetermined film thickness is formed on the power supply film that is formed on the upper face of the silicon substrate, using a spin coater or the like. The resist is exposed through a photo mask that has a predetermined pattern formed thereon, and is processed for development. The resist image is thereby formed.

The conditions for coating the resist film are as follows.
Resist Agent: A novolac-based resin+an organic solvent
Number of Rotations of Spin Coater: 1,130 rpm
Thickness of Resist Film: 2 μm The resist agent is coated on the upper face of the silicon substrate using the spin coater. The solvent is thereafter vaporized at 130° C. in a nitrogen atmosphere and the resist agent is thereafter cooled. The resist film is thereby formed.

The resist agent is exposed by applying a light beam at an energy density of 2,500 J/m$^2$ and including a wavelength of 365 nm for 0.25 sec.

The exposed portion is brought into contact with an alkaline solution to be processed for development.

<Formation of Filter Base Body Part>

The filter base body parts 14 are formed each in an opening portion of the resist image. The filter base body parts 14 each including a nickel-plated film are formed using an electrolytic plating method, using the power supply film formed in advance as the power supply source.

The conditions for forming the filter base body parts 14 are as follows.

Pre-Process: The surface of the power supply film is activated by being immersed in diluted sulfuric acid for 60 seconds.
Plating Solution: Nickel sulfamate plating solution, solution temperature of 55° C. and pH=4.0
Plating Rate: 0.5 μm/min
Plating: Electrolytic plating is conducted shaking the work.

<Dissolution and Peeling off of Resist>

The resist is removed by dissolving the resist film by applying an ultrasonic wave to the filter base body parts 14 in an acetone solution for 15 minutes.

<Formation of Supporting Base Material>

For conducting the filtering using the filter 10, a supporting base material may be disposed in the filter 10 when necessary.

Figure 4:
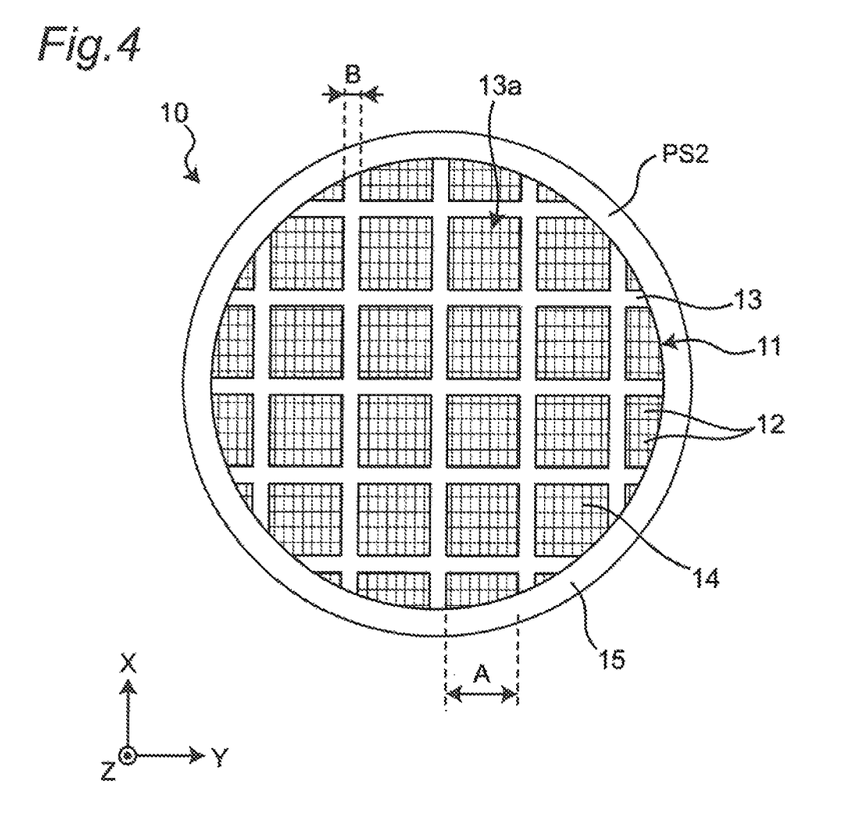
FIG. 4 is a schematic diagram of the state where a supporting base material is disposed on the filter of the first embodiment according to the present invention.

FIG. 4 depicts a schematic configuration of the filter 10 to which the supporting base material 13 is attached. As depicted in FIG. 4, the supporting base material 13 may be disposed on the side of the second principal surface PS2 of the filter 10. Plural square opening portions 13a are disposed in the supporting base material 13. The thickness of the supporting base material 13 is, for example, 14 μm and one side of the opening portion 13a, that is, each of the intervals A of the crosspieces is 260 μm and the width B of the crosspiece is 14 μm.

Any breakage of the filter 10 can be prevented during the filtering by disposing the supporting base material 13 as above. The supporting base material is fabricated at the following steps.

A photo sensitive resist is again coated on the upper face of the silicon substrate that has the base bodies of the filter 10 formed thereon, to form a resist film. The resist is thereafter exposed through a photo mask to be processed for development. A resist image is thereby formed. In this case, the exposure and the process for development are conducted such that the resist image extends over plural base bodies of the filter 10. The portion for the resist image to extend over the base bodies of the filter 10 becomes the opening portion of the filter 10 after completion of the filter 10. The number of the base bodies of the filter 10 over which the resist image extends is properly determined in accordance with the aperture ratio required to the filter 10.

The filter base body parts 14 are formed in the opening portions of the resist image. The supporting base material including a nickel-plated film is formed using an electrolytic plating method, using the power supply film formed in advance as the power supply source. The width of the supporting base material is properly determined in accordance with the strength required to the filter 10.

The resist is peeled off by dissolving the resist film by applying an ultrasonic wave to the supporting base material in an acetone solution for 15 minutes.

<Removal of Power Supply Film>

The power supply film is removed, and the filter base body parts 14 and the supporting base material are separated from the silicon substrate to thereby complete the filter 10 for filtering nucleated cells.

The removal of the power supply film is conducted by immersing the power supply film in a water solution produced by mixing a 60%-hydrogen peroxide water solution, acetic acid, and pure water with each other at mixing ratios of 1:1:20 for 48 hours under the condition of 25° C.

[Effects]

According to the filter 10 of the first embodiment, the following effects can be achieved.

The filter 10 includes at least either a metal or a metal oxide as its main component. The filter 10 includes the filter part 11 that has the plural through holes 12 formed therein. With this configuration, the through holes 12 of the filter part 11 tend to avoid being deformed, the nucleated cells to be trapped can be trapped, and the collection rate of the nucleated cells can be improved.

The longitudinal diameter of the inscribed ellipse of the through hole 12 is designed to be smaller than the size of the nucleus of each of the nucleated cells. With this configuration, the collection rate of the nucleated cells can further be improved.

The shape of the through hole 12 is formed to be a rectangle. With this configuration, the time period for the filtering can be reduced compared to a through hole having a square shape. Describing in detail, the cytoplasm of a nucleated cell tends to be deformed compared to the nucleus thereof. With the through hole having the square shape, when the nucleated cell is trapped by the filter part, the cytoplasm thereof may be deformed and the through hole may be clogged by the deformed cytoplasm. On the other hand, with the through hole 12 having the rectangular shape, in the case where the nucleated cell is trapped, even when the cytoplasm is deformed and clogs a portion of the through hole 12, the liquid can pass through the through hole 12 from the other portion. The through hole 12 having the rectangular shape therefore tends to cause the liquid to pass therethrough and the time period for the filtering can be reduced compared to the through hole having the square shape.

The first principal surface PS1 of the filter part 11 is formed to be flat and smooth. With this configuration, the nucleated cells trapped by the first principal surface PS1 can easily be separated from the filter part 11 and the collection thereof therefore becomes simple.

Various shapes such as an ellipsoidal shape are present in addition to an exact circular shape as the shapes of the nuclei of the nucleated cells. For the filter 10, the longitudinal diameter of the inscribed ellipse of the through hole 12 is formed to be smaller than the size of the nucleus of each of the nucleated cells, and the inscribed ellipse of the through hole 12 is an ellipse butting all the sides that define the opening of the through hole 12. With this configuration, nuclei having various shapes other than the nucleus having the exact circular shape can reliably be trapped and the collection rate thereof can be improved.

With the filtering method using the filter 10, the nucleated cells to be trapped can reliably be trapped by causing the liquid containing the nucleated cells to pass through the filter 10, and the collection rate can therefore be improved.

As to the nucleated cell, the size of the nucleus thereof varies depending on the type, the culturing conditions, the passage number, and the like. For example, even for same cells, the sizes of the nuclei thereof differ from each other depending on the culturing conditions such as the temperature for the culturing, the time period therefor, the environment therefor, or the like. Even same nucleated cells have nuclei whose sizes therefore have a wide variety and, when the filter 10 is prepared without noting the sizes of the nuclei, the nucleated cells may pass through the through holes 12. In the filtering method using the filter 10, the filter 10 is prepared whose through holes 12 have the size selected in accordance with the size of the nuclei of the nucleated cells. In the filtering method using the filter 10, the filter 10 whose through holes 12 are smaller than the size of the nuclei of the nucleated cells to be trapped is selected and the filter 10 to be used for the filtering is thereby prepared. With the filtering method using the filter 10, the nucleated cells can therefore be reliably trapped on the filter 10 and the collection rate thereof can be improved.

The example where the dimensions of the through holes 12 are substantially equal has been described in the first embodiment while the dimensions are not limited to the above. For example, the dimensions of the through holes 12 may differ from each other. In this case, the greatest dimension of the through holes 12 only has to be designed to be smaller than the size of the nucleus of each of the nucleated cells.

The example where the manufacturing method for the filter 10 includes the step of forming the supporting base material 13 has been described in the first embodiment while the manufacturing method is not limited to the above. For example, the manufacturing method for the filter 10 may not include the step of forming the supporting base material 13.

The example where the liquid containing the nucleated cells is caused to pass through the filter 10 has been described in the first embodiment while the filtering is not limited to the above. For example, living cells and dead cells may be separated from each other from a liquid containing the living cells and the dead cells using the filter 10.

For example, the living cells may be trapped on the first principal surface PS1 of the filter part 11 by the filter 10 and the dead cells may be caused to pass therethrough as the method of separating the living cells and the dead cells. The dead cells may be trapped on the first principal surface PS1 of the filter part 11 by the filter 10 and the living cells may be caused to pass therethrough.

The filter 10 and the filtering method have been described in the first embodiment while the filter 10 and the filtering method are not limited to the above. For example, the filter 10 and the filtering method may be used as a kit to conduct the filtering method, that includes the filter 10 for filtering nucleated cells.

The example where the filter part 11 has the uniform film thickness has been described in the first embodiment while the film thickness of the filter part 11 is not limited to the above. For example, the filter part 11 may be formed not to have a uniform film thickness but to have the film thickness on the side of the center thereof to be smaller compared to that on the side of the peripheral edge thereof.

Figure 5:
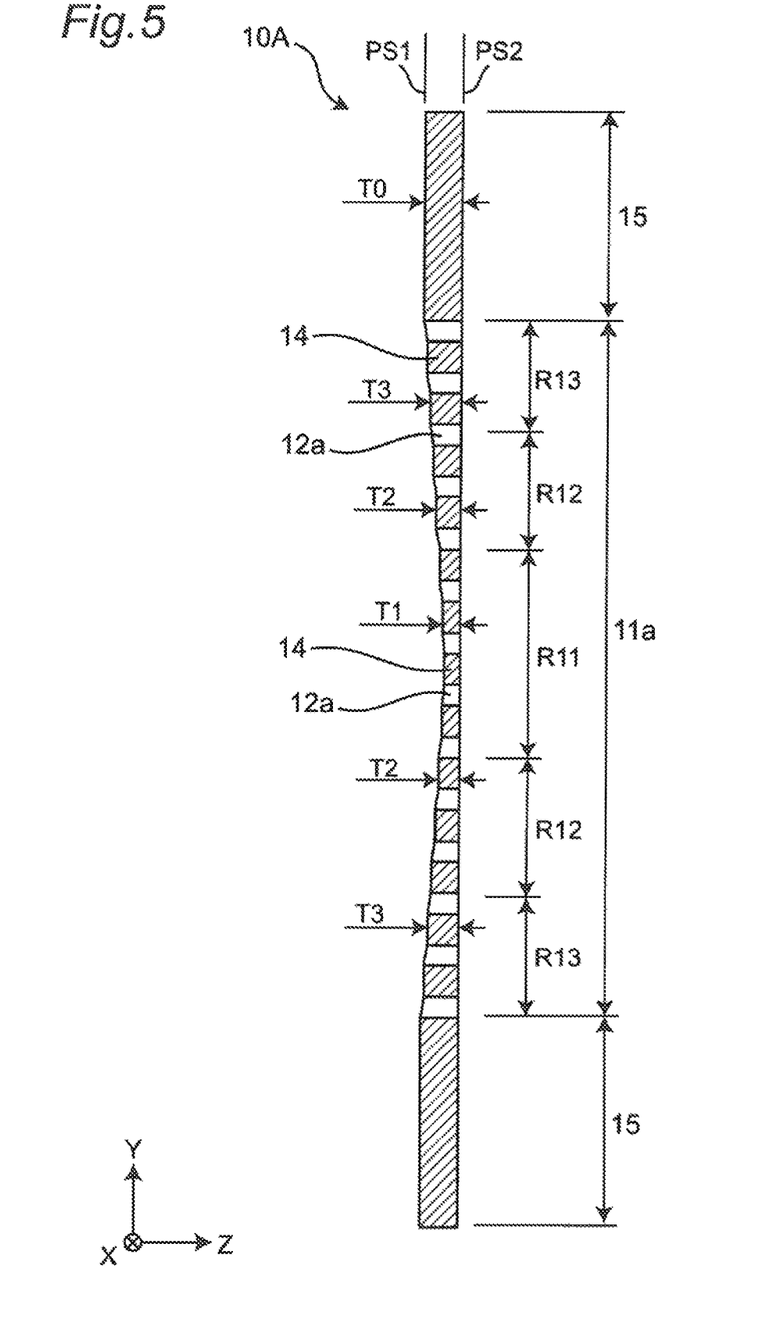
FIG. 5 is a schematic diagram of a filter of a modification example of the first embodiment according to the present invention.

FIG. 5 depicts a filter 10A of a modification example of the first embodiment. As depicted in FIG. 5, in a filter part 11a of the filter 10A, a film thickness T1 in a region R11 on the side of the center distant from the frame part 15 is formed to be smaller than a film thickness T3 in a region R13 on the peripheral edge closer to the frame part 15 than to the region R11 on the side of the center. As to the filter 10A, in the filter part 11a, denoting the film thickness in an intermediate region R12 positioned between the region R11 on the side of the center and the region R13 on the side of the peripheral edge as T2, the film thicknesses in these regions satisfy the relation T1<T2<T3. In the filter part 11a of the filter 10, the film thickness is set such that the film thickness increases from the center of the filter part 11a toward the radial direction (outward in the radius direction). The film thickness may be set to increase continuously or stepwise.

As depicted in FIG. 5, the second principal surface PS2 of the filter 10A is formed as a flat face and a face corresponding to the filter part 11a in the first principal surface PS1 is formed to be a concave face whose region on the peripheral edge is higher than a region thereof on the side of the center. The frame part 15 of the filter 10A is formed for a film thickness T0 thereof to have a substantially constant thickness and the film thickness T0 is equal to or greater than the film thickness T3 in the region R13 on the side of the peripheral edge.

The filter 10A is formed to have, for example, a diameter of 6 mm (the outer shape of the frame part 15), the width dimension of 1 mm of the frame part 15, and the interval between adjacent through holes 12a of 1 μm to 500 μm. The filter part 11a is formed such that the film thickness T3 in the region R13 on the peripheral edge close to the frame part 15 is 1.1 μm and the film thickness T1 in the region R11 on the side of the center is 0.8 μm.

According to the filter 10A, in the filter part 11a, the first principal surface PS1 is formed as a concave face such that the film thickness T1 of the region R11 on the side of the center is smaller than the film thickness T3 in the region R13 on the side of the peripheral edge. A fluid reservoir thereby tends to be formed in the concave face by the surface tension of the fluid when the cells are trapped by the first principal surface PS1 having the concave face formed thereon. Processes such as an analysis can be conducted suppressing any drying of the cells by handling the cells trapped in the state, for example, where the culture liquid is accumulated in the concave face as a fluid reservoir. Handling convenience of the cells trapped by the filter part 11a can be improved.

In the filter part 11a, a smooth concave face can be formed in the filter part 11a by setting the film thickness of the filter part 11a to increase continuously or stepwise from the region R11 on the side of the center toward the region R13 on the side of the peripheral edge. The formation of the fluid reservoir can thereby be facilitated in the concave face by the action of the surface tension and handling convenience of the cells trapped by the filter part 11a can be improved.

The second principal surface PS2 of the filter part 11a is formed to be the flat face and the first principal surface PS1 is formed to be the concave face. For example, when the fluid reservoir using the concave face is desired to be used, the cells can be trapped on the side of the first principal surface PS1 that is the concave face. On the other hand, when the passage condition of the fluid is desired to be improved without forming the fluid reservoir, the cells can be trapped on the side of the second principal surface PS2 that is the flat face. Handling convenience of the cell filtering filter can be improved by using the proper one of the first principal surface PS1 and the second principal surface PS2 in accordance with the purpose as above.

In the description for the filter 10A, the case where the concave face is formed such that the film thickness increases continuously or stepwise from the region R11 on the side of the center toward the region R13 on the side of the peripheral edge in the filter part 11a has been taken as the example. The filter 10A is however not limited only to the above case. For example, the case may be employed where a portion having the film thickness increasing therein from the region R11 on the side of the center toward the region R13 on the side of the peripheral edge is included in the filter part 11a. Even in this case, the effects of the filter 10A can be achieved only when the average film thickness in the region R11 on the side of the center is smaller than the average film thickness in the region R13 on the peripheral edge.

The example where the shape of the through hole 12 is a rectangular shape has been described in the first embodiment while the shape of the through hole 12 is not limited to the above. For example, the shape of the through hole 12 may be any one of polygonal shapes except a square shape.

Figure 6:
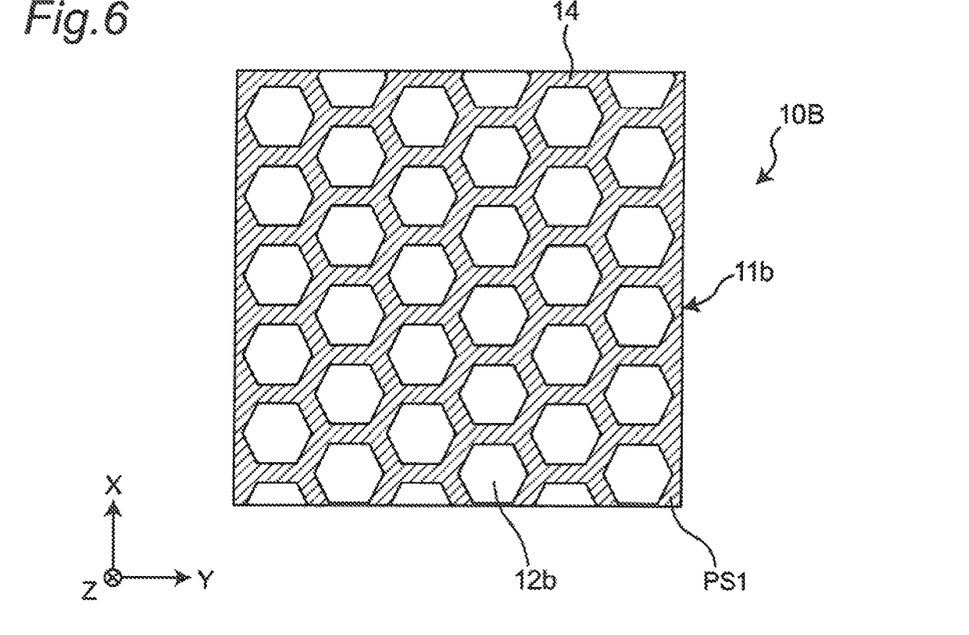
FIG. 6 is an enlarged cross-sectional diagram of a portion of a filter of another modification example of the first embodiment according to the present invention.

FIG. 6 depicts an enlarged cross-sectional diagram of a portion of a filter 10B that includes through holes 12b each formed to have a regular hexagonal shape. As depicted in FIG. 6, the plural through holes 12b each formed to have the regular hexagonal shape are formed in a regular triangle grid arrangement (a honeycomb structure) in the filter part 11b of the filter 10B.

Figure 7:
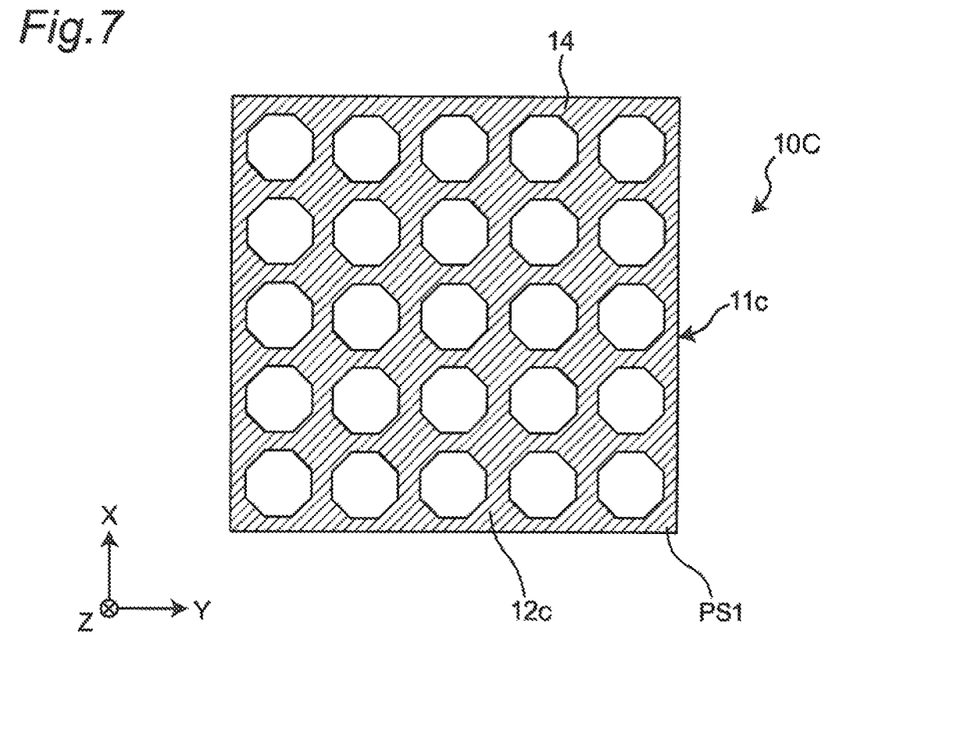
FIG. 7 is an enlarged cross-sectional diagram of a portion of a filter of yet another modification example of the first embodiment according to the present invention.

FIG. 7 depicts an enlarged cross-sectional diagram of a portion of a filter 10C that includes through holes 12c each formed to have a regular octagonal shape. As depicted in FIG. 7, the plural through holes 12c each formed to have the regular octagonal shape are formed in a square grid in the filter part 11c of the filter 10C.

As depicted in FIG. 6 and FIG. 7, for each of the through holes 12b and 12c each having the regular polygonal shape, the angle between adjacent two of the sides that define the opening of each of the through holes 12b and 12c may be set to be an obtuse angle. The corner portions of each of the through holes 12a and 12b are each set to be mild compared to a through hole having the square shape. An advantage is therefore established that the through holes 12b and 12c each tend to avoid damaging any cell compared to the through hole having the square shape. The through holes 12b and 12c each having the regular polygonal shape are each easily processed compared to the through hole having the square shape and the processing precision thereof can therefore be improved. The through holes 12b and 12c each having the polygonal shape can reduce the variation coefficient compared to the through hole having the square shape.

The through hole 12 may be formed to have a regular polygonal shape other than the regular hexagonal shape and the regular octagonal shape.

Figure 8:
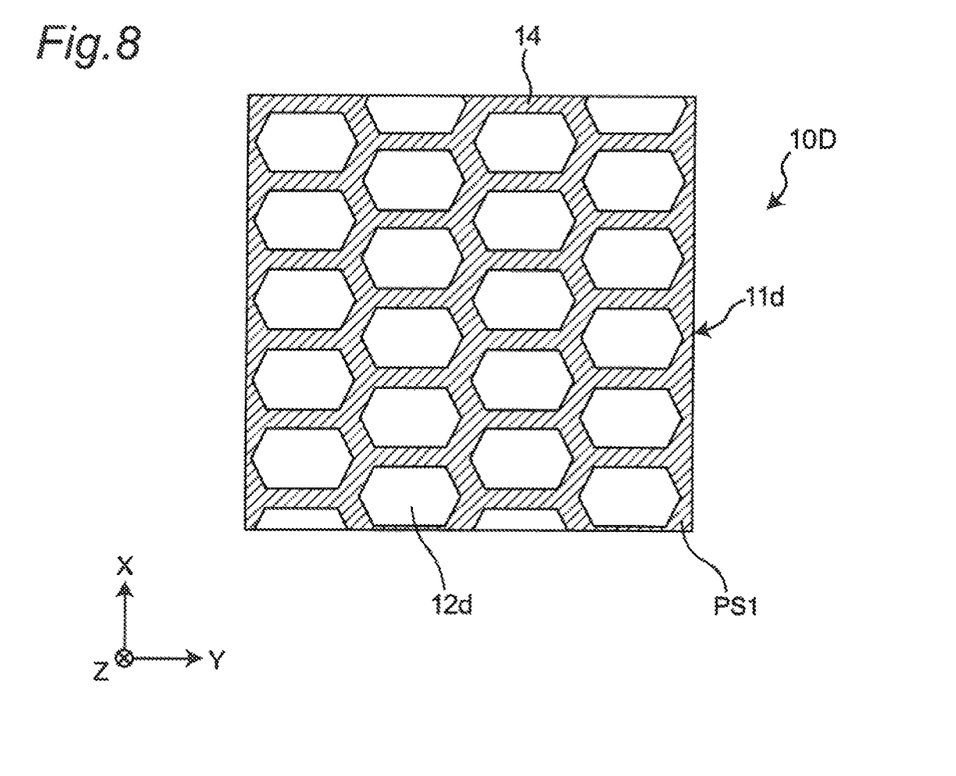
FIG. 8 is an enlarged cross-sectional diagram of a portion of a filter of yet another modification example of the first embodiment according to the present invention.

The shape of the through hole 12 may be a polygonal shape that includes sides having different lengths. FIG. 8 depicts an enlarged cross-sectional diagram of a portion of a filter 10D that has through holes 12d formed therein each to have a polygonal shape. As depicted in FIG. 8, in the filter 10D, the through holes 12d are each formed to have a laterally long hexagonal shape that is elongated in the Y-direction. For example, the through holes 12d are each formed to have a laterally long hexagonal shape whose two sides defining the opening and parallel to each other are elongated in the Y-direction.

With this configuration, the filter 10D can achieve the same effects as those of the through holes 12b and 12c each having the regular polygonal shape and can achieve the same effects as those of the through holes 12 each having the rectangular shape.

For the filter 10D, the through holes 12d are not limited to the through holes 12d each having the hexagonal shape and through holes 12d each having a polygonal shape such as an octagonal shape may be employed. The direction for the through holes 12d of the filter 10D to be elongated is not limited. For example, the through holes 12d may each be formed to have a longitudinally long polygonal shape elongated in the X-direction.

EXAMPLES

Evaluation of the performance of the filter 10 according to the first embodiment was conducted using Examples 1 to 5 and Comparative Examples 1 to 3.

(1) Filters of Examples 1 to 5 and Comparative Examples 1 to 3

The filters of Examples 1 to 5 and Comparative Examples 1 to 3 were manufactured in accordance with the specifications shown in Table 1.

TABLE 1

|  | Example 1 | Example 2 | Example 3 | Example 4 |
|---|---|---|---|---|
| Hole Shape | Rectangular shape | Rectangular shape | Regular hexagonal shape | Regular octagonal shape |
| Hole Size (μm) | Long side: 3.0 Shor side: 2.5 | Long side: 3.5 Short side: 1.9 | One side: 1.9 | One side: 1.4 |
| Longitudinal Diameter of Inscribed Ellipse (μm) | 3.0 | 3.5 | 3.3 | 3.4 |
| Lateral Diameter of Inscribed Ellipse (μm) | 2.5 | 1.9 | — | — |
| Standard Deviation of Longitudinal Diameter of Inscribed Ellipse | 0.3 | 0.4 | 0.3 | 0.3 |
| Standard Deviation of Lateral Diameter of Inscribed Ellipse | 0.3 | 0.2 | — | — |
| Variation Coefficient of Longitudinal Diameter of Inscribed Ellipse | 0.12 | 0.12 | 0.11 | 0.11 |
| Variation Coefficient of Lateral Diameter of Inscribed Ellipse | 0.12 | 0.11 | — | — |
| Hole Arrangement Form | Rectangular grid | Rectangular grid | Regular triangle grid | Square grid |
| Arrangement Interval (Pitch) (μm) | Long side: 4.0 Short side: 3.5 | Long side: 4.5 Short side: 2.9 | 4.3 | 4.24 |
| Aperture Ratio (%) | 53.6 | 51.0 | 57.8 | 50.0 |
| Number of Holes ($\times 10^6$ holes) | 2.01 | 2.16 | 1.90 | 1.50 |
| Cross-Sectional Shape | Flat plate | Flat plate | Flat plate | Flat plate |
| Thickness at Center of Filter (μm) | 1.00 | 0.97 | 0.96 | 1.04 |
| Thickness in Vicinity of Outer Circumference of Filter (μm) | 1.15 | 1.09 | 1.05 | 1.14 |

|  | Example 5 | Comparative Example 1 | Comparative Example 2 | Comparative Example 3 |
|---|---|---|---|---|
| Hole Shape | Rectangular shape | Rectangular shape | Regular hexagonal shape | Regular octagonal shape |
| Hole Size (μm) | Long side: 3.0 Shor side: 2.5 | Long side: 9.0 Short side: 2.5 | One side: 3.8 | One side: 2.7 |
| Longitudinal Diameter of Inscribed Ellipse (μm) | 3.0 | 9.0 | 6.6 | 6.5 |
| Lateral Diameter of Inscribed Ellipse (μm) | 2.5 | 2.5 | — | — |

TABLE 1-continued

| | | | | |
|---|---|---|---|---|
| Standard Deviation of Longitudinal Diameter of Inscribed Ellipse | 0.3 | 0.3 | 0.3 | 0.3 |
| Standard Deviation of Lateral Diameter of Inscribed Ellipse | 0.3 | 0.3 | — | — |
| Variation Coefficient of Longitudinal Diameter of Inscribed Ellipse | 0.12 | 0.10 | 0.10 | 0.10 |
| Variation Coefficient of Lateral Diameter of Inscribed Ellipse | 0.12 | 0.12 | — | — |
| Hole Arrangement Form | Rectangular grid | Rectangular grid | Regular triangular grid | Square grid |
| Arrangement Interval (Pitch) (μm) | Long side: 4.0 Short side: 3.5 | Long side: 10.0 Short side: 3.5 | 7.6 | 8.2 |
| Aperture Ratio (%) | 53.6 | 64.3 | 74.6 | 50.0 |
| Number of Holes (×10$^6$ holes) | 2.01 | 0.80 | 0.61 | 0.41 |
| Cross-Sectional Shape | Concave plate | Flat plate | Flat plate | Flat plate |
| Thickness at Center of Filter (μm) | 1.01 | 1.72 | 1.02 | 1.09 |
| Thickness in Vicinity of Outer Circumference of Filter (μm) | 1.41 | 1.71 | 1.10 | 1.11 |

As to the arrangement interval in Table 1, the long side corresponded to the length denoted by the reference numeral b1 in FIG. 3, and the short side corresponded to the length denoted by b2 in FIG. 3.

Each of the filters of Examples 1 to 5 and Comparative Examples 1 to 3 had the circular shape and the diameter of the outer shape of the filter was 7.8 mm. The diameter of the filter part 11 thereof was 6 mm. The thickness of the frame part thereof was 2 μm. The material thereof was nickel (Ni).

In each of Examples 1 and 2, the filter 10 was used that included the through holes 12 each having the rectangular shape. In Example 3, the filter 10B was used that included the through holes 12b each having the regular hexagonal shape. In Example 4, the filter 10C was used that included the through holes 12 each having the regular octagonal shape. In Example 5, the filter 10A was used that included the through holes 12a each having the rectangular shape. In Example 5, the film thickness of the filter part 11a in the region on the side of the center, distant from the frame part 15 was smaller than the film thickness of the filter part 11a in the region on the side of the peripheral edge, closer to the frame part 15 than to the region on the side of the center.

In Comparative Example 1, the filter 10 was used that included the through holes 12 each having the rectangular shape. In Comparative Example 2, the filter 10B was used that included the through holes 12b each having the regular hexagonal shape. In Comparative Example 3, the filter 10C was used that included the through holes 12c each having the regular octagonal shape.

Each of the filters of Examples 1 to 5 and Comparative Examples 1 to 3 was installed in a filtering apparatus and a cell suspension was filtered to thereby conduct evaluation of the performance. Each of the filters was immersed in an ethanol solution for one minute and was thereafter immersed in pure water for one minute to enhance the hydrophilicity thereof as a pre-process.

(2) Cell Suspension

Suspended cells HL-60 to each be a leukemia cell strain were cultured for five days on an RPMI 1620 culture medium (including L-glutamine) that included 10-vol % fetal bovine serum and 1-vol % penicillin-streptomycin, using a 100-mm dish.

A portion of a culture liquid was moved from the 100-mm dish to a 15-mL centrifugal tube by pipetting. Centrifugal separation was conducted for the centrifugal tube that had therein the culture liquid at the number of rotations of 1,000 rpm and for three minutes to thereafter remove the supernatant liquid therefrom. A phosphate buffered physiological saline solution was added to the residue to produce a cell suspension. The amount of the added phosphate buffered physiological saline solution was adjusted to set the cell concentration of the cell suspension to be 10$^5$ cell/mL.

30 μL of the cell suspension and 15 μL of a fluorescent reagent DAPI were mixed with each other using a micro tube to dye the cells. The dyed cell suspension (a cell stain liquid) was incubated for 20 minutes at 37° C. in a dark state. 10 μL of the cell stain liquid was thereafter dripped onto a glass slide and a cover glass was put on over the glass slide. A fluorescent observation was conducted through a bandpass filter centering 455 nm using a fluorescence microscope and using an excitation light source having a wavelength of 345 nm. Measurement of the size of a nucleus developing a blue-purple color presented 3.66 μm as the size of the nucleus of HL-60. The size of the nucleus of HL-60 was an average value calculated by measuring the sizes of the nuclei of 100 cells of HL-60.

The cells were dispersed by pipetting in a portion of the culture liquid in the 100-mm dish and 10 μL was thereafter taken out therefrom using a micro pipet to measure the cell concentration, the survival rate, the average value of the size of the cell using a cell counter (an automatic cell counter "Countess" (a registered trademark) II FL manufactured by Thermo Fisher). As a result, the cell concentration was 5×10$^5$ cell/mL, the average value of the size of the active cell (HL-60) was 13.4 μm and the survival rate was 90%. For example, the cell suspension and a 0.4%-trypan-blue solution were mixed with each other at volume ratios of 1:1 to dye the cell membranes to be blue. 10-μL of the mixture liquid of the cell suspension and the trypan-blue solution was dripped onto a cell counting slide ("Countess" (a registered trademark) Cell Counting Chamber Slide manufactured by Thermo Fisher) to observe the form of the cells. In the cell-counting, the number of the cells (the concentration), the average value of the size of the cell, and the survival rate were determined by an image analysis using the dyed cell membranes as markers.

An RPMI 1620 culture medium was further mixed with the culture liquid in the 100-mm dish at optional ratios and the following HL-60 cell suspension was thereby prepared.

The concentration of active cells (HL-60) . . . $3.06 \times 10^5$ cell/mL

The liquid amount . . . 1 mL

The survival rate of the cells was measured using the above method for the culture liquid in the 100-mm dish that had been left for four hours in a clean bench at the room temperature and, as a result, the survival rate was reduced to 81%. This means that the activity was degraded by leaving the cells for a long time at the room temperature.

(3) Filtering Method

For each of the filters of the Examples 1 to 5 and Comparative Examples 1 to 3 that was attached to the filtering apparatus, the cell suspension was dripped on the first principal surface PS1 of the filter part 11 using a pipet and the cell suspension was suctioned from the side of the second principal surface PS2 to thereby conduct filtering of the cell suspension. Suction was conducted at a pressure of 0.5 kPa as the condition for the operation. As soon as the fact that the amount of the liquid passing through the filter (a passage liquid) became about 0.8 mL was confirmed by visual observation, the suction was discontinued. The evaluation was conducted by measuring the time period from the start of the suction to the discontinuation of the suction (a time period for filtering), the liquid amount of the passage liquid, and the number of the cells contained in the passage liquid.

(4) Result of Evaluation

Table 2 shows the result of the evaluation.

TABLE 2

|  | Example 1 | Example 2 | Example 3 | Example 4 |
|---|---|---|---|---|
| Cell | HL-60 | | | |
| Number of Input Active Cells ($\times 10^5$ cells) | 5.01 | | | |
| Liquid Amount (ml) | 1.0 | | | |
| Time Period for Filtering (sec) | 14 | 8 | 32 | 27 |
| Liquid Amount of Passage Liquid (ml) | 0.82 | 0.84 | 0.88 | 0.78 |
| Number of Cells Contained in Passage Liquid ($\times 10^5$ cells) | 0 | 0 | 0 | 0 |
| Collection Rate (%) | 100 | 100 | 100 | 100 |

|  | Example 5 | Comparative Example 1 | Comparative Example 2 | Comparative Example 3 |
|---|---|---|---|---|
| Cell | HL-60 | | | |
| Number of Input Active Cells ($\times 10^5$ cells) | 5.01 | | | |
| Liquid Amount (ml) | 1.0 | | | |
| Time Period for Filtering (sec) | 11 | 1 | 2 | 4 |
| Liquid Amount of Passage Liquid (ml) | 0.77 | 0.92 | 0.88 | 0.9 |
| Number of Cells Contained in Passage Liquid ($\times 10^5$ cells) | 0 | 3.54 | 3.22 | 2.96 |
| Collection Rate (%) | 100 | 29.3 | 35.7 | 40.9 |

In each of Examples 1 to 5, the collection rate of the cells (HL-60) was 100%. In contrast, in Comparative Examples 1 to 3, the collection rates of the cells were respectively 29.3%, 35.7%, and 40.9%.

As shown in Table 1, in Comparative Examples 1 to 3, the longitudinal diameters of the inscribed ellipses of the through holes 12 were respectively 9.0 µm, 6.6 µm, and 6.5 µm and were larger than the size of the nucleus of the cell (HL-60) of 3.66 µm. It is considered that the cells passed through the through holes 12.

On the other hand, for each of Examples 1 to 5, the longitudinal diameter of the inscribed ellipse of the though hole 12 was 3.0 µm to 3.5 µm and was smaller than the size of the nucleus of the cell. It is therefore considered that the cells were able to reliably be trapped in Examples 1 to 5.

In this specification, the "collection rate" means the rate of the number of the input active cells to the number of cells trapped on the first principal surface PS1 of the filter and was calculated in accordance with (the number of the input active cells—the number of the active cells contained in the passage liquid)/(the number of the input active cells).

As to the number of the active cells contained in the passage liquid, the cells in the passage liquid were dispersed by pipetting and 10 specimens each of 10 µL of the passage liquid were thereafter taken out therefrom using a micro pipet to measure the number of the cells in each of the specimens using a cell counter (an automatic cell counter "Countess" (a registered trademark) II FL manufactured by Thermo Fisher).

The collection rate can be improved by designing the longitudinal diameter of the inscribed ellipse of the through hole 12 to be smaller than the size of the cell nucleus as above. The reason for this is that the cytoplasm surrounding the cell nucleus tends to be deformed and the cell nucleus tends to avoid being deformed.

In the case where the longitudinal diameter of the inscribed ellipse of the through hole 12 is greater than the size of the cell nucleus as in Comparative Examples 1 to 3, even when the longitudinal diameter of the inscribed ellipse of the through hole 12 is smaller than the size of the overall cell, the cell may pass through the filter 10 due to deformation of the cytoplasm.

On the other hand, when the longitudinal diameter of the inscribed ellipse of the through hole 12 is designed to be smaller than the cell nucleus as in Examples 1 to 5, because the cell nucleus tends to avoid being deformed compared to the cytoplasm, the cells tend to be trapped on the filter 10 compared to Comparative Examples 1 to 3.

The fact that the filter 10 is made from a metal also contributes to the improvement of the collection rate of the cells. The amount of deformation of the through hole 12 itself of the filter 10 is reduced compared to that of the filter made from a resin such as a membrane by using the filter 10 made from a metal. The filter 10 therefore further easily traps the cells.

Not to mention, preferably, mixing of any impurity with the cell suspension, that is, any elution of the metal constituting the filter 10 into the cell suspension is suppressed during the filtering of the nucleated cells.

In Example 5, after the filtering, the cells trapped on the first principal surface PS1 of the filter part 11a were observed. As a result, it turned out that, similar to the cells before filtering, the form of the cell was a circular shape and the activity thereof was maintained. This was because a fluid reservoir was formed in the region R11 on the side of the center of the filter part 11a and the cells were trapped on the first principal surface PS1 of the filter part 11a in the state where the cells were immersed in the fluid reservoir.

Measurement of the immersion potential to be an index of the ionization tendency of a metal was conducted for nickel. The immersion potential in a phosphate buffered physiological saline solution relative to a reference electrode including silver chloride immersed in a saturated potassium chloride solution was measured for three minutes and, as a result, the immersion potential of nickel transitioned in a range that was nobler than 0.03 V. It can be stated that a metal and/or a metal oxide that present(s) an immersion potential nobler than at least 0.03 V measured under the same conditions enable(s) filtering without degrading the activity of the cells.

In Examples 1, 2, and 5, the time periods for the filtering were short compared to those of Examples 3 and 4. This is because the through holes 12 were each formed to have the rectangular shape and any clogging due to deformation of the cytoplasm of each of the cells was able to thereby be suppressed. For example, in the case where the shape of the through hole 12 was the rectangular shape, even when a portion of the through hole 12 was clogged due to the deformation of the cytoplasm, the liquid tended to pass through the through hole 12 from the other portion. It is considered that the time periods for the filtering were reduced in Examples 1, 2, and 5 compared to those in Examples 3 and 4.

The example where the nucleated cells were trapped by filtering the cell suspension whose concentration was relatively high to have nucleated cells equal to or more than $10^5$ cell/mL present in the cell suspension has been described in Examples while the filter 10 can trap the nucleated cells to be collected even when a cell suspension whose concentration is extremely low to have nucleated cells of about several cell/mL in the cell suspension is filtered.

The present invention has been fully described in relation to the preferred embodiment with reference to the accompanying drawings while various changes and various modifications thereof are obvious to those skilled in the art. It should be understood that those changes and modifications are encompassed therein within the scope not departing from the present invention described in the appended claims.

The filter of the present invention can improve the collection rate of nucleated cells and is therefore useful for a use of separating the nucleated cells from a cell suspension.

EXPLANATIONS OF LETTERS OR NUMBERS 10, 10A, 10B, 10C, 10D: filter
11, 11a, 11b, 11c, 11d: filter part
12, 12a, 12b, 12c, 12d: through hole
13: supporting base material
13a: opening portion
14: filter base body part
15: frame part
PS1: first principal surface
PS2: second principal surface
R11: region on the side of the center
R12: intermediate region
R13: region on the side of the peripheral edge
T0, T1, T2, T3: film thickness

The invention claimed is:

1. A filter for filtering nucleated cells, the filter comprising:
 a body having a first principal surface and a second principal surface that face each other, the body containing at least a metal as a main component thereof or a metal oxide as a main component thereof, and the body defining a plurality of through holes penetrating from the first principal surface to the second principal surface, each of the plurality of through holes having a shape other than a square shape, wherein
 a longitudinal diameter of an ellipse inscribed within each of the plurality of through holes is smaller than a size of a nucleus of each of the nucleated cells to be filtered,
 the ellipse inscribed within each of the plurality of through holes abuts all sides of the through hole within which the ellipse is inscribed,
 wherein the body comprises a filter part and a frame part, and the frame part is arranged to surround an outer circumference of the filter part,
 wherein the first principal surface consists of a first side of the frame part, a second side of the frame part, and a first side of the filter part, and the first side of the filter part is located immediately between the first side of the frame part and the second side of the frame part,
 wherein the second principal surface consists of a third side of the frame part, a fourth side of the frame part, and a second side of the filter part, and the second side of the filter part is located immediately between the third side of the frame part and the fourth side of the frame part,
 wherein the first side of the frame part and the third side of the frame part face each other,
 wherein the second side of the frame part and the fourth side of the frame part face each other,
 wherein the first side of the filter part and the second side of the filter part face each other, and
 wherein the entire first side of the filter part is in the shape of a concave face such that the filter part has a film thickness that decreases toward a center of the filter part, and the concave face is configured to form a fluid reservoir which suppresses drying of the nucleated cells to be filtered.

2. The filter according to claim 1, wherein each of the plurality of through holes has a polygonal shape.

3. The filter according to claim 2, wherein the polygonal shape is a rectangular shape.

4. The filter according to claim 1, wherein the second principal surface has a flat shape.

5. The filter according to claim 1, wherein the at least the metal or the metal oxide has an immersion potential in a phosphate buffered physiological saline solution, that is nobler than 0.03 V relative to that of a reference electrode comprising silver chloride, immersed in a saturated potassium chloride solution.

6. The filter according to claim 1, wherein the at least the metal or the metal oxide comprises at least one selected from gold, silver, copper, platinum, nickel, palladium, an alloy thereof, and an oxide thereof.

7. The filter according to claim 1, wherein an outer surface layer of the filter includes the metal or the metal oxide.

8. A filtering method for filtering nucleated cells, the method comprising:
 preparing a filter body having a first principal surface and a second principal surface that face each other, the filter body comprising at least a metal as a main component thereof or a metal oxide as a main component thereof, and the body defining a plurality of through holes penetrating from the first principal surface to the second principal surface, each of the plurality of through holes having a shape other than a square shape, wherein a longitudinal diameter of an ellipse inscribed within each of the plurality of through holes is smaller than a size of a nucleus of the nucleated cell to be filtered, the ellipse inscribed within each of the plurality of through holes abuts all sides of the through hole within which the ellipse is inscribed, and wherein the body comprises a filter part and a frame part, and the frame part is arranged to surround an outer circumference of the filter part, wherein the first principal surface consists of a first side of the frame part, a second side of the frame part, and a first side of the filter part, and the first side of the filter part is located immediately between the first side of the frame part and the second side of the frame part, wherein the second principal surface consists of a third side of the frame part, a fourth side of the frame part, and a second side of the filter part, and the second side of the filter part is located immediately between the third side of the frame part and the fourth side of the frame part, wherein the first side of the frame part and the third side of the frame part face each other, wherein the second side of the frame part and the fourth side of the frame part face each other, wherein the first side of the filter part and the second side of the filter part face each other, and wherein the entire first side of the filter part is in the shape of a concave face such that the filter part has a film thickness that decreases toward a center of the filter part, and the concave face is configured to form a fluid reservoir which suppresses drying of the nucleated cells to be filtered; and causing a liquid containing the nucleated cells to pass through the plurality of through holes of the filter body.

9. The filtering method according to claim 8, wherein each of the plurality of through holes has a polygonal shape.

10. The filtering method according to claim 9, wherein the polygonal shape is a rectangular shape.

11. The filtering method according to claim 8, wherein the second principal surface has a flat shape.

12. The filtering method according to claim 8, wherein the at least the metal or the metal oxide has an immersion potential in a phosphate buffered physiological saline solution, that is nobler than 0.03 V relative to that of a reference electrode comprising silver chloride, immersed in a saturated potassium chloride solution.

13. The filtering method according to claim 8, wherein the at least the metal or the metal oxide comprises at least one selected from gold, silver, copper, platinum, nickel, palladium, an alloy thereof, and an oxide thereof.

14. The filtering method according to claim 8, wherein the causing of the liquid containing the nucleated cells to pass through the plurality of through holes of the filter body causes the separation of living cells and dead cells from each other.

15. The filtering method according to claim 8, wherein an outer surface layer of the filter includes the metal or the metal oxide.

* * * * *